(12) United States Patent
Campbell

(10) Patent No.: US 7,884,620 B2
(45) Date of Patent: Feb. 8, 2011

(54) SENSOR FOR MEASURING MOISTURE AND SALINITY

(75) Inventor: Jeffrey Campbell, Horseshoe Bend, ID (US)

(73) Assignee: Green Badge, LLC, King of Prussia, PA (US)

( * ) Notice: Subject to any disclaimer, the term of this patent is extended or adjusted under 35 U.S.C. 154(b) by 0 days.

(21) Appl. No.: 12/465,620

(22) Filed: May 13, 2009

(65) Prior Publication Data

US 2009/0219037 A1 Sep. 3, 2009

Related U.S. Application Data

(60) Division of application No. 12/185,083, filed on Aug. 2, 2008, now Pat. No. 7,535,237, and a continuation-in-part of application No. 12/124,977, filed on May 21, 2008, now Pat. No. 7,408,364.

(60) Provisional application No. 61/022,362, filed on Jan. 21, 2008.

(51) Int. Cl.
*G01R 27/26* (2006.01)
*G01R 27/08* (2006.01)

(52) U.S. Cl. .............. 324/644; 324/689; 324/690; 324/694; 324/696; 324/713

(58) Field of Classification Search ........... 324/649, 324/658, 663–665, 679, 684, 686, 689–691, 324/694, 696, 713; 73/74; 137/78.3; 700/284; 702/62

See application file for complete search history.

(56) References Cited

U.S. PATENT DOCUMENTS

| 3,323,047 | A |   | 5/1967  | Martin et al.            |
|-----------|---|---|---------|--------------------------|
| 4,540,936 | A |   | 9/1985  | Walsh                    |
| 5,179,347 | A | * | 1/1993  | Hawkins .......... 324/696 |
| 5,418,466 | A |   | 5/1995  | Watson et al.            |
| 5,424,649 | A | * | 6/1995  | Gluck et al. ...... 324/667 |
| 5,445,178 | A |   | 8/1995  | Feuer                    |
| 5,479,104 | A |   | 12/1995 | Cambell                  |
| 5,859,536 | A | * | 1/1999  | Stockton .......... 324/664 |
| 6,014,029 | A | * | 1/2000  | Soto et al. ...... 324/664 |
| 7,042,234 | B2|   | 5/2006  | Buss                     |
| 7,129,713 | B2|   | 10/2006 | Katz                     |
| 2006/0178847 | A1 | * | 8/2006 | Glancy et al. ...... 702/62 |

* cited by examiner

*Primary Examiner*—Timothy J Dole
(74) *Attorney, Agent, or Firm*—Clause Eight IPS; Michael Catania

(57) ABSTRACT

A sensor for measuring the moisture and salinity of a material is disclosed herein. The sensor preferably includes a soil moisture circuit, a soil salinity circuit and a probe structure. The soil moisture circuit includes a high frequency oscillator, a voltage meter and a reference capacitor. The soil salinity circuit includes a low frequency oscillator, a voltage meter and a reference resistor. A third voltage meter allows for voltage outputs to be measured to calculate soil moisture and soil salinity values.

5 Claims, 11 Drawing Sheets

| Water (%) | 01 | 02 | 03 | 01' | 02' | 02" | 03" | RP | RC |
|---|---|---|---|---|---|---|---|---|---|
| 40.2% | 0.439 | 0.438 | 0.44 | 2.47 | 1.176 | 2.171 | 2.69 | 0.3632 | 0.7702 |
| 36.5% | 0.43 | 0.429 | 0.432 | 2.5 | 1.23 | 2.16 | 2.683 | 0.3866 | 0.7690 |
| 33.2% | 0.433 | 0.432 | 0.433 | 2.56 | 1.342 | 2.144 | 2.684 | 0.4286 | 0.7606 |
| 30.4% | 0.424 | 0.423 | 0.424 | 2.59 | 1.429 | 2.141 | 2.678 | 0.4653 | 0.7622 |
| 27.8% | 0.43 | 0.429 | 0.432 | 2.62 | 1.517 | 2.185 | 2.684 | 0.4964 | 0.7798 |
| 25.3% | 0.437 | 0.434 | 0.437 | 2.7 | 1.668 | 2.208 | 2.689 | 0.5453 | 0.7877 |
| 22.6% | 0.437 | 0.435 | 0.438 | 2.73 | 1.774 | 2.236 | 2.689 | 0.5845 | 0.8001 |
| 20.6% | 0.438 | 0.437 | 0.438 | 2.75 | 1.838 | 2.266 | 2.691 | 0.6060 | 0.8118 |
| 18.1% | 0.433 | 0.43 | 0.433 | 2.73 | 1.883 | 2.303 | 2.681 | 0.6326 | 0.8332 |
| 16.4% | 0.429 | 0.427 | 0.428 | 2.74 | 1.923 | 2.351 | 2.68 | 0.6462 | 0.8544 |
| 14.4% | 0.429 | 0.428 | 0.429 | 2.81 | 2.039 | 2.407 | 2.69 | 0.6777 | 0.8753 |
| 12.3% | 0.432 | 0.429 | 0.432 | 2.82 | 2.092 | 2.453 | 2.694 | 0.6961 | 0.8948 |
| 10.1% | 0.443 | 0.441 | 0.444 | 2.82 | 2.143 | 2.471 | 2.703 | 0.7163 | 0.8968 |
| 8.7% | 0.443 | 0.441 | 0.444 | 2.81 | 2.161 | 2.514 | 2.703 | 0.7282 | 0.9177 |
| 7.3% | 0.435 | 0.433 | 0.435 | 2.79 | 2.144 | 2.531 | 2.698 | 0.7259 | 0.9271 |
| 4.8% | 0.424 | 0.422 | 0.424 | 2.82 | 2.186 | 2.547 | 2.691 | 0.7356 | 0.9374 |
| 3.1% | 0.44 | 0.438 | 0.44 | 2.86 | 2.319 | 2.603 | 2.707 | 0.7760 | 0.9550 |
| 1.5% | 0.433 | 0.432 | 0.434 | 2.88 | 2.397 | 2.673 | 2.705 | 0.8037 | 0.9868 |
| 0.1% | 0.429 | 0.428 | 0.429 | 2.89 | 2.418 | 2.672 | 2.701 | 0.8099 | 0.9877 |
| 0.0% | 0.437 | 0.435 | 0.437 | 2.89 | 2.423 | 2.683 | 2.707 | 0.8111 | 0.9903 |

202

| Sensor Set | Sensor | Media | O2 | O3 | O2" | O3" | RC |
|---|---|---|---|---|---|---|---|
| I | A | 0.1 Ds/M | 0.433 | 0.434 | 1.157 | 2.646 | 0.3237 |
| | B | 0.1 | 0.434 | 0.433 | 1.158 | 2.645 | 0.3273 |
| | C | 0.1 | 0.434 | 0.433 | 1.158 | 2.645 | 0.3273 |
| | D | 0.1 | 0.43 | 0.429 | 1.154 | 2.642 | 0.3272 |
| II | C | 0.2 | 0.433 | 0.432 | 1.005 | 2.639 | 0.2592 |
| | D | 0.2 | 0.429 | 0.429 | 1.002 | 2.636 | 0.2596 |
| | A | 0.2 | 0.433 | 0.433 | 1.004 | 2.64 | 0.2587 |
| | B | 0.2 | 0.43 | 0.435 | 1.002 | 2.644 | 0.2589 |
| III | B | 0.39 | 0.43 | 0.435 | 0.787 | 2.635 | 0.1623 |
| | C | 0.39 | 0.433 | 0.432 | 0.793 | 2.63 | 0.1638 |
| | D | 0.39 | 0.429 | 0.428 | 0.788 | 2.628 | 0.1632 |
| | A | 0.39 | 0.433 | 0.433 | 0.791 | 2.631 | 0.1629 |
| IV | C | 0.77 | 0.432 | 0.432 | 0.642 | 2.624 | 0.0958 |
| | D | 0.77 | 0.429 | 0.428 | 0.638 | 2.622 | 0.0953 |
| | A | 0.77 | 0.432 | 0.433 | 0.64 | 2.625 | 0.0949 |
| | B | 0.77 | 0.429 | 0.434 | 0.638 | 2.629 | 0.0952 |
| V | C | 1.41 | 0.43 | 0.43 | 0.55 | 2.619 | 0.0548 |
| | B | 1.41 | 0.429 | 0.434 | 0.548 | 2.625 | 0.0543 |
| | D | 1.41 | 0.429 | 0.428 | 0.548 | 2.618 | 0.0543 |
| | A | 1.41 | 0.432 | 0.432 | 0.55 | 2.622 | 0.0539 |
| VI | A | 2.06 | 0.432 | 0.433 | 0.506 | 2.62 | 0.0338 |
| | B | 2.06 | 0.429 | 0.434 | 0.502 | 2.623 | 0.0333 |
| | D | 2.06 | 0.429 | 0.429 | 0.502 | 2.615 | 0.0334 |
| | C | 2.06 | 0.432 | 0.43 | 0.506 | 2.618 | 0.0338 |
| VII | C | 2.65 | 0.432 | 0.43 | 0.485 | 2.618 | 0.0242 |
| | D | 2.65 | 0.429 | 0.428 | 0.482 | 2.615 | 0.0242 |
| | A | 2.65 | 0.432 | 0.432 | 0.484 | 2.619 | 0.0238 |
| | B | 2.65 | 0.429 | 0.434 | 0.483 | 2.623 | 0.0247 |
| VIII | C | 3.4 | 0.43 | 0.43 | 0.467 | 2.617 | 0.0169 |
| | D | 3.4 | 0.427 | 0.427 | 0.463 | 2.614 | 0.0165 |
| | B | 3.4 | 0.429 | 0.434 | 0.465 | 2.622 | 0.0165 |
| | A | 3.4 | 0.43 | 0.432 | 0.467 | 2.618 | 0.0169 |
| IX | B | 4.18 | 0.428 | 0.434 | 0.455 | 2.622 | 0.0123 |
| | A | 4.18 | 0.432 | 0.432 | 0.457 | 2.618 | 0.0114 |
| | D | 4.18 | 0.428 | 0.427 | 0.454 | 2.613 | 0.0119 |
| | C | 4.18 | 0.432 | 0.429 | 0.457 | 2.615 | 0.0114 |
| X | C | 4.96 | 0.43 | 0.43 | 0.45 | 2.615 | 0.0092 |
| | D | 4.96 | 0.427 | 0.427 | 0.446 | 2.613 | 0.0087 |
| | A | 4.96 | 0.43 | 0.432 | 0.449 | 2.617 | 0.0087 |
| | B | 4.96 | 0.428 | 0.433 | 0.446 | 2.62 | 0.0082 |

| Sensor Set | Parameter | Value |
|---|---|---|
| I | Ave | 0.3273 |
| I | StDev (%) | 0.02% |
| II | Ave | 0.2591 |
| II | StDev (%) | 0.15% |
| III | Ave | 0.1630 |
| III | StDev (%) | 0.39% |
| IV | Ave | 0.0953 |
| IV | StDev (%) | 0.40% |
| V | Ave | 0.0543 |
| V | StDev (%) | 0.71% |
| VI | Ave | 0.0336 |
| VI | StDev (%) | 0.79% |
| VII | Ave | 0.0242 |
| VII | StDev (%) | 1.50% |
| VIII | Ave | 0.0167 |
| VIII | StDev (%) | 1.61% |
| IX | Ave | 0.0118 |
| IX | StDev (%) | 3.68% |
| X | Ave | 0.0087 |
| X | StDev (%) | 4.33% |

301

302

SENSOR FOR MEASURING MOISTURE AND SALINITY

CROSS REFERENCE TO RELATED APPLICATION

The present application is a divisional application of U.S. patent application Ser. No. 12/185,083, filed Aug. 2, 2008, which is a continuation application of U.S. patent application Ser. No. 12/124,977, filed on May 21, 2008, now U.S. Pat. No. 7,408,364, and claims priority to U.S. Provisional Patent Application No. 61/022,362, filed on Jan. 21, 2008.

STATEMENT REGARDING FEDERALLY SPONSORED RESEARCH OR DEVELOPMENT

Not Applicable

BACKGROUND OF THE INVENTION

1. Field of the Invention

The present invention related to a sensor for measuring the moisture content and salinity of a material. More specifically, the present invention relates to a sensor for measuring the moisture content and salinity of soil.

2. Description of the Related Art

The prior art discusses several soil monitoring sensors.

There have been several sensor approaches to measuring the moisture and salinity of soil. One such approach is described by U.S. Pat. No. 5,479,104 (the '104 patent). The sensor of the '104 patent uses one oscillator and one frequency, a bridge type scheme with two resistors functioning as reference bridge elements, and three AC meters to measure the unknown capacitance of the soil ($C_s$) and resistance of the soil ($R_s$), where the capacitance can be directly related to soil moisture and the resistance to salinity. The use of such a sensor requires the following steps: powering the sensor (which turns on the oscillator); reading the three AC meters; performing numerous calculations to determine $C_s$ and $R_s$; applying calibration equations to convert $C_s$ to soil moisture measurements and $R_s$ to salinity measurements; and turning off the sensor.

The difficulty with such a sensor scheme is that the calculations to determine $C_s$ and $R_s$ are very complex relations of two ratios: (1) AC Meter 3/AC Meter 1 and (2) AC Meter 2/AC Meter 1. These calculations are particularly complex in actual systems with higher order effects present, thus requiring the use of complex number equations.

A further difficulty is that AC meters that operate at such high frequencies are difficult and expensive. This problem is often addressed by using simple diode detectors in place of standard AC meters. Diode detectors, however, become highly non-linear when the AC voltage lowers to around 0.2 volts such that it becomes difficult to relate the DC meter voltage reading to the actual AC voltage level being measured. At such voltages, the detectors also become increasingly sensitive to variations in the components used. Further, the diode detectors display a significant temperature dependence that requires correction.

Referring to the '104 patent, the basic scheme is shown in FIG. 2 of the '104 patent. To begin with, in the '104 patent, one frequency is used, 50 MHz in the built version of that sensor. It employs a bridge type scheme with R1 and R2 as known reference bridge elements, along with three AC meters to measure the unknown capacitance and resistance of the soil (element 24). The capacitance can be directly related to soil moisture and the resistance to salinity. The calculations to determine Cs and Rs are very complex (particularly in actual systems with higher order effects present) relations of two ratios—(AC Meter 3/AC Meter 1) and (AC Meter 2/AC Meter 1). Essentially there are two measured ratios which are then used to solve for two unknowns—Cs, Rs. The simpler first order calculations are shown in the patent (column 6, near line 50).

The actual steps in the measurement process are as follows: power the sensor (which activates the oscillator), read the three AC meters, perform the calculations to obtain the Cs value to soil moisture and Rs value to salinity, and then deactivate the sensor.

Because AC meters that operate at these high frequencies are difficult and expensive, simple diode detectors are used as a proxy for AC meters. These are shown in FIG. 3 of the '104 patent. The output of these meters is a DC voltage read by the DC Meters. The DC meters are inexpensive, but have problems. Once the AC voltage gets low (around 0.2 volts or so), the detectors stop working well. Even at AC voltages around 0.3V, the detectors become highly non-linear (i.e. it is not easy to relate the DC Meter to the actual AC voltage level being measured) and the detectors become increasingly sensitive to component variations (the diode, resistor, and capacitor used). In addition, these detectors also display a significant temperature dependence that needs to be corrected for in the measurement. At the end of the line, the calculations needed to correct for detector temperature effects and non-linearity, as well as calculating Cs and Rs including the higher order effects, which becomes very complicated.

To provide accurate moisture and salinity measurements, therefore, current sensors must calculate capacitances and resistances, including higher order effects, using very complicated complex number equations that can also correct detector temperature effects and detector non-linearity.

Thus, there is need for a sensor to measure the capacitance and resistance of soil that uses simpler calculations, provides improved detector performance, and, ultimately, provides more accurate moisture and salinity measurements.

BRIEF SUMMARY OF THE INVENTION

The present invention relates to a sensor monitor and a method thereof to resolve the issues associated with the sensor monitors of the prior art.

One aspect of the present invention is a method of determining a moisture content value and a salinity value of a soil, the method begins with providing a sensor. The sensor includes a probe conducting structure to be placed in the soil to form a capacitor, a soil moisture circuit and a soil salinity circuit. The soil moisture circuit includes a high frequency oscillator for applying a first electrical stimulus to the probe structure, a reference capacitor connected in series to the high frequency oscillator, and a first voltage meter located between the high frequency oscillator and the reference capacitor. The soil salinity circuit includes a low frequency oscillator for applying second electrical stimulus to the probe structure, a reference resistor connected in series to the low frequency oscillator, and a second voltage meter located between the low frequency oscillator and the reference resistor. The low frequency oscillator is substantially lower in frequency than the high frequency oscillator. The soil salinity circuit and the soil moisture circuit are connected between the reference capacitor and the reference resistor, at which point the soil moisture circuit and the soil salinity circuit are connected to the probe structure and a third voltage meter.

The method also includes measuring voltages V1, V2, and V3, wherein V1 is the output voltage measured by the first voltage meter when the low frequency oscillator and the high frequency oscillator are inactive, V2 is the output voltage measured by the second voltage meter when the low frequency oscillator and the high frequency oscillator are inactive, and V3 is the output voltage measured by the third voltage meter when the low frequency oscillator and the high frequency oscillator are inactive. The method also includes measuring voltages V2' and V3', wherein V2' is the output voltage measured by the second voltage meter when the low frequency oscillator is active and the high frequency oscillator is inactive, and V3' is the output voltage measured by the third voltage meter when the low frequency oscillator is active and the high frequency oscillator is inactive. The method also includes measuring voltages V1' and V3", wherein V1' is the output voltage measured by the first voltage meter when the low frequency oscillator is inactive and the high frequency oscillator is active, and V3" is the output voltage measured by the third voltage meter when the low frequency oscillator is inactive and the high frequency oscillator is active. The method also includes calculating a capacitance of the soil as a function of (V3"−V3)/(V1'−V1) to obtain a soil moisture content value. The method also includes calculating a resistance of the soil as a function of (V3'−V3)/(V2'−V2) to obtain a soil salinity value.

The critical difference between the sensor of the present invention and the sensor of the '104 patent lies in the fact that two separate bridge circuits and frequencies are used and that the soil moisture leg uses a capacitor for a reference element while the soil conductivity leg uses a resistor.

There are a number of advantages. By using a capacitor as the bridge element in measuring the capacitance (soil moisture) and a resistor in the bridge circuit for measuring soil conductivity (or resistance-related to salinity), the bridge circuit should be "tuned" appropriately. By using the appropriate bridge element in each leg, there are two benefits: 1) better resolution and accuracy in the measurement of the unknown value; and 2) greatly simplified mathematical algorithms to calculate the desired quantities. Third, the AC meter of the present invention is vastly improved.

The measurement process is as follows (note that, while not shown, in the sensor of the present invention there is a digital signal processor (a microcontroller) that can turn on and off the oscillators as well as measure the DC voltages produced by the detectors). First, both oscillator 1 and 2 are turned off and the voltage of all the detectors is measured (referred to as V1, V2, and V3 for AC meters 1 through 3 respectively). The low frequency oscillator 2 is turned on and the detector voltages for AC meter 3 and 2 are measured (V3' and V2'). Oscillator 2 is then turned off, and the high frequency oscillator 1 is turned on and the voltages of AC meter 1 and 2 are measured (V1' and V2'). It can then be shown that, due to the careful design of the circuit, that:

$$Cs = f(\text{Ratio } HF), Rs = g(\text{Ratio } LF)$$

Where: Ratio HF=(V2"−V2)/(V1'−V1) Ratio LF=(V2'−V2)/(V3'−V3)

In general these functions are simple polynomials that include all the higher order effects. This data reduction is much simpler than in the sensor of the '104 patent. Also note that the measurement of capacitance is not affected by the resistance present within the soil (within typical ranges) and similarly, the resistance is not affected by the capacitance present. This is achieved by the "tuned" bridge circuit and careful choice of component values.

Returning to the AC meter embodiment used in the sensor of the present invention, it should be noted that the biasing that has been added dramatically improves the detector performance. The presence of the bias voltage allows the detector output to be measured in the absence of any AC signal being present in the circuit. This allows the sensors to be "tared" and captures the variation in components in the detector and temperature drifts. It is not possible to do this with the sensor of the '104 patent, the diodes must be carefully matched (i.e. have the same critical properties which isn't easy and can be a manufacturing nightmare) and complicated and somewhat uncertain temperature corrections applied. In addition, the biased detectors have the advantage of being able to respond to very small AC signals and are much more accurate at low AC signal levels. Since the individual detectors are tared, they don't require carefully matched parts as well making manufacturing easier.

The invention overcomes difficulties encountered in the prior art by using two separate bridge circuits and frequencies to measure the moisture and salinity of soil, where a soil moisture bridge circuit uses a capacitor for a reference element and a soil salinity bridge circuit uses a resistor for a reference element. Campbell, U.S. patent application Ser. No. 12/185,083, filed Aug. 2, 2008, is hereby incorporated by reference in its entirety.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

Figure 1:
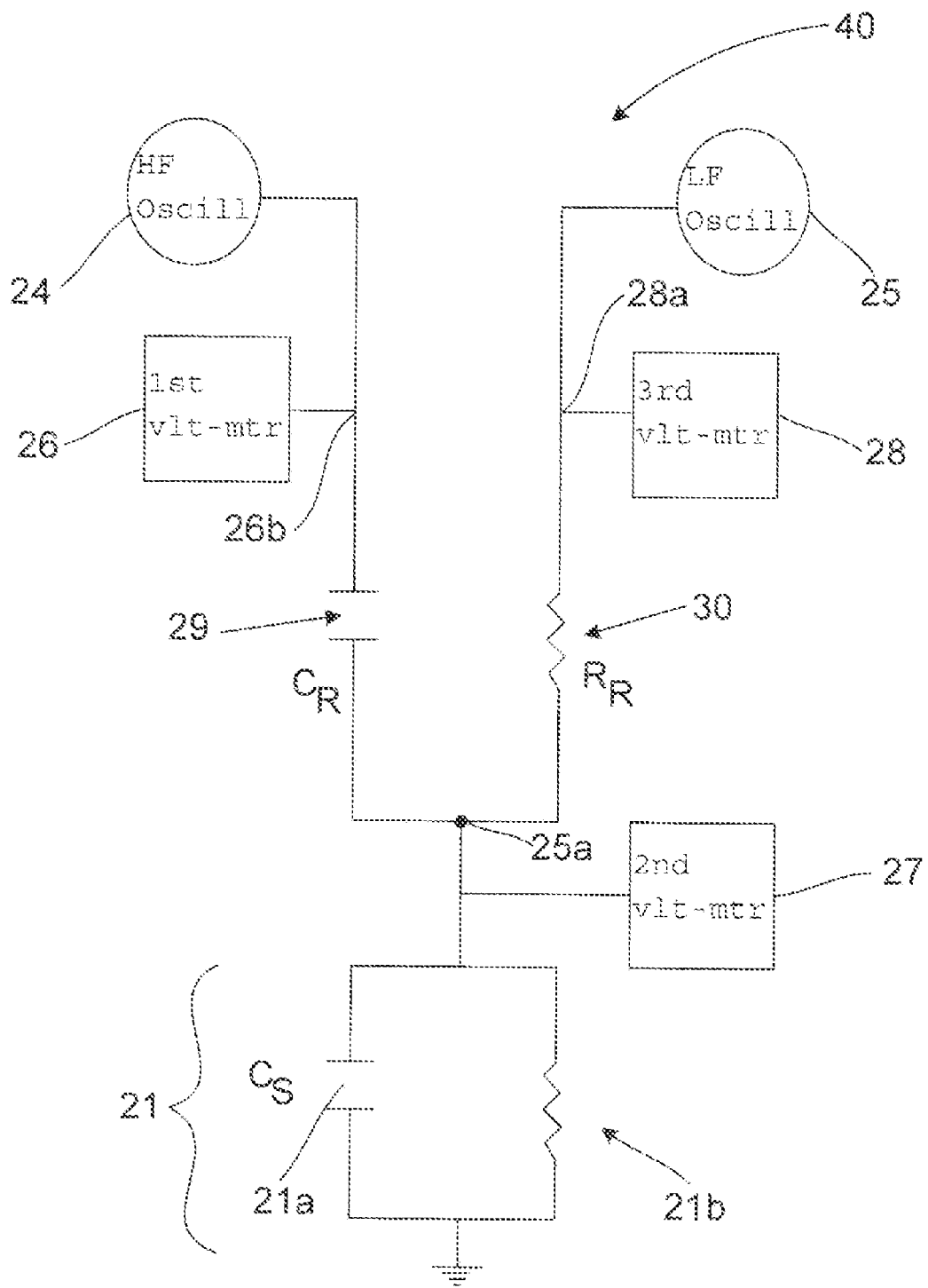
FIG. 1 illustrates a preferred embodiment of the circuitry of the sensor of the present invention.
Figure 1A:
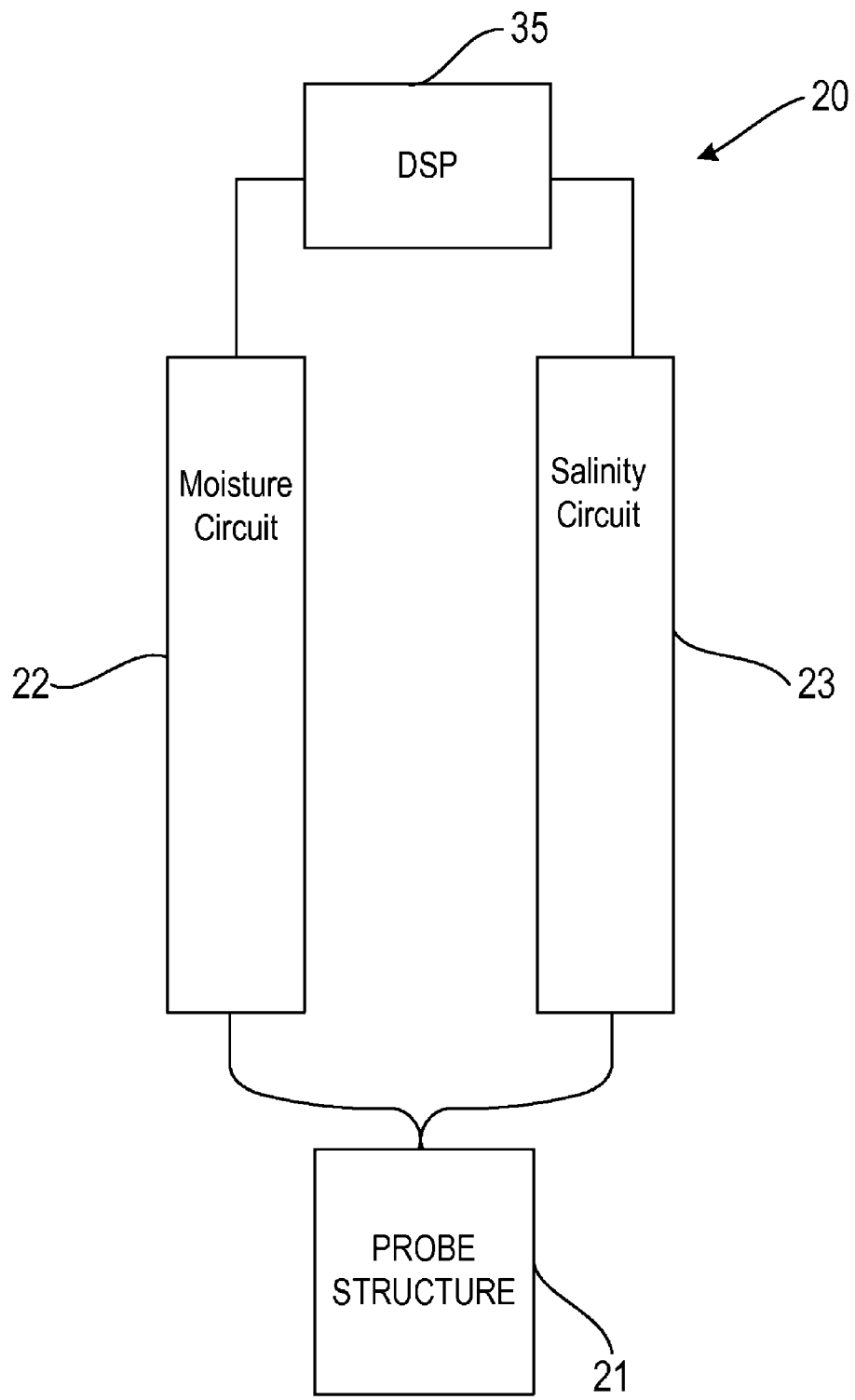
FIG. 1A is a block diagram of a sensor of the present invention.
Figure 2:
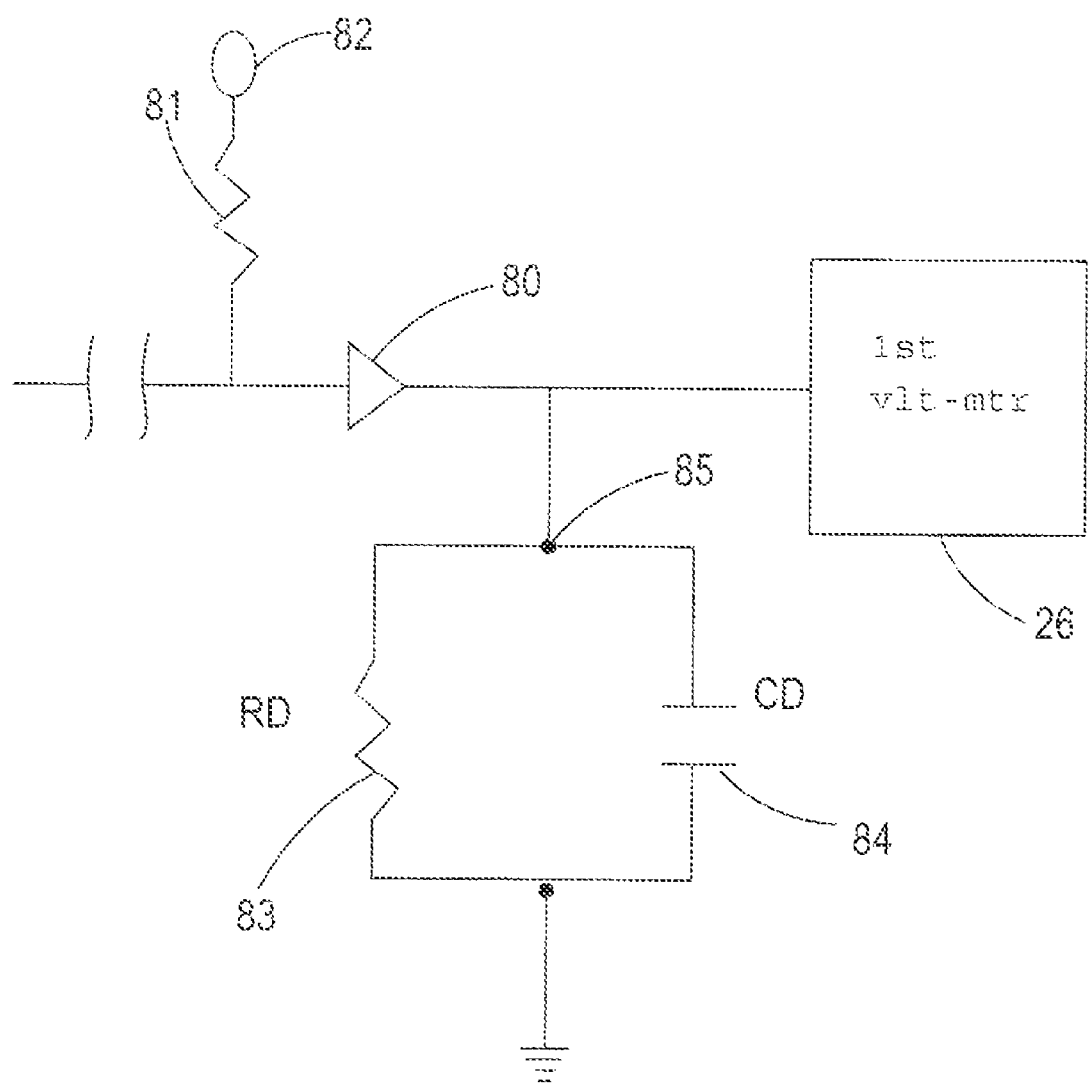
FIG. 2 illustrates an embodiment of a biased diode detector used by the invention as an AC meter.

FIG. 1 illustrates a circuit diagram of a preferred embodiment of the circuit 40 of the sensor apparatus 20 of the present invention. FIG. 2 illustrates a detailed circuit diagram of a preferred section of the circuit 40. FIG. 1A is a block diagram of the sensor apparatus 20. As shown in FIG. 1A, the sensor apparatus 20 preferable includes a digital signal processor 35 connected to a moisture circuit 22 and a salinity circuit 23, which are both connected to a probe structure 21.

The probe structure 21 is placed in the soil which is to be measured. The probe structure 21 forms an effective coaxial capacitor within the soil. Such probe structures are well known in the art, and typically include a base and elongated conductors extending from the base and disposed around a central elongated conductor. The digital signal processor 35 or microprocessor, facilitates the process, allowing for multiple conducting structures to be inserted into the soil (or other media of interest) as well as cabling to provide power and transfer measurement results to recording or control instrumentation. The probe structure 21, which when placed in soil forms, electrically, the circuit elements $C_S$ 21a and $R_s$ 21b as shown in FIG. 1, and are referred to as forming a "capacitor." The probe structure 21 can be arranged in a variety of different geometries many of which are shown in U.S. Pat. Nos. 2,870,404, 4,288,742, and 4,540,936, all of which are hereby incorporated by reference in their entireties. The conducting structures of the afore-mentioned '104 patent can also be included in the present invention a probe structure 21. The probe structure 21 can be made of metal, printed circuit board, or other electrically conductive materials. Depending on the media of interest, the range of expected $C_S$ and $R_s$ to be measured and frequencies employed, many different geometries and sizes can be employed as the probe structure 21 in sensor.

FIG. 1 shows an embodiment of the circuit 40 of the sensor 20 of the present invention. As illustrated in FIG. 1A, the sensor 20 uses two separate bridge circuits and frequencies that coexist together without significantly perturbing each other. The soil moisture circuit 22 preferably includes, as shown in FIG. 1, a high frequency oscillator 24, a first voltage meter 26, and a reference capacitor $C_R$ 29 of a known value. The soil salinity circuit 23 preferably includes, as shown in FIG. 1, a low frequency oscillator 25, a third voltage meter 28, and a reference resistor $R_R$ 30 of a known value. The circuits 22 and 23 share a second voltage meter 27, as well as the probe structure 21 positioned in the soil, the electrical equivalent of which is represented by the lower circuitry of FIG. 1 and designated $C_S$ 21a and $R_s$ 21b. In this embodiment of the invention, each of the first voltage meter 26, the second voltage meter 27 and the third voltage meter 28 is preferably an alternating current ("AC") voltage meter. As shown in FIG. 2, on one end a diode 80 is connected to a resistor $R_D$ 83 and capacitor $C_D$ 84, as well the voltage meter 26. On another end, the diode 80 is connected to a bias resistor 81 with a biased output voltage 82.

The measurement process is as follows. First, the oscillators 24 and 25 are deactivated and voltages V1, V2, and V3 are measured, where V1, V2, and V3 are the voltages at the first voltage meter 26, the second voltage meter 27 and the third voltage meter 28, respectively, when the oscillators 24 and 25 are deactivated. Next, the low frequency oscillator 25 is activated and voltages V2' and V3' are measured, where voltages V2' and V3' are the voltages at the second voltage meter 27 and the third voltage meter 28, respectively, when only the low frequency oscillator 25 is activated. Next, the low frequency oscillator 25 is deactivated, and the high frequency oscillator 24 is activated, and voltages V1' and V3" are measured, where voltages V1' and V3" are the voltages at the first voltage meter 26 and the third voltage meter 28, respectively, when only the high frequency oscillator 24 is activated.

The capacitance of the soil is a function of the ratio of the high frequency ("HF") voltage measurements, and the resistance of the soil is a function of the ratio of the low frequency ("LF") voltage measurements:

The following equations demonstrate the afore-mentioned:

$$C_s = f(\text{Ratio } HF)$$

$$R_s = f(\text{Ratio } LF)$$

Where: Ratio HF=(V3"−V3)/(V1'−V1)

and Ratio LF=(V3'−V3)/(V2'−V2)

Note that, while not shown, a person of ordinary skill would understand to use devices such as a digital signal processor 35 or a microcontroller to activate and deactivate the oscillators 24 and 25, as well as measure the voltages produced by the first voltage meter 26, the second voltage meter 27 and the third voltage meter 28.

The present invention provides multiple advantages over the prior art. For example, when attempting to measure soil moisture, the present invention uses a high frequency oscillator 24, but when measuring soil salinity the present invention uses a low frequency oscillator 25.

To accommodate both measurements, other sensors use a compromise middle frequency. Such a compromise, however, limits the accuracy and range of measurement of the sensor. The dual circuits 22 and 23 of the present invention avoid this compromise by enabling the application of both high and low frequencies. Second, by using a capacitor as the bridge element in measuring the soil's capacitance ($C_s$) and a resistor as the bridge element in measuring soil's resistance ($R_s$), the bridge circuit is "tuned" appropriately in that the soil capacitance can be determined with the least error introduced by the soil resistance, and conversely, the soil resistance can be determined with the least error introduced by the soil capacitance. That is, the bridge elements provide that the $C_s$ and $R_s$ can be compared to a comparable $C_R$ and $R_R$.

By using the appropriate bridge element in each circuit, the invention provides better resolution and accuracy in the measurement of the unknown values and greatly simplified mathematical algorithms to calculate the desired quantities. Higher order effects in practical sensors such as stray capacitance, can be handled using relatively simple polynomials. The simplicity of this sensor, as opposed for example to the embodiment described in the '104 patent, arises from the "tuned" nature of the circuits which allow soil capacitance and resistance effects to be separately determined without any mutual interaction. Thus, the functions described above are simple polynomials that include all the higher order effects, and therefore enable significantly simpler data reduction.

Further, the tuned bridge circuit and a careful choice of component values ensures that the measurement of capacitance does not affect the resistance present within the soil (within typical ranges) and, similarly, the measurement of resistance does not affect the capacitance present.

FIG. 2 illustrates an embodiment of a biased diode voltage meter used by the invention as an AC voltage meter. The diode voltage meters measure a peak voltage present in the circuit 40 (subject to some correction and temperature compensation) and are related to the root mean square (RMS) voltage present in the case of sinusoidal voltages. Standard RMS AC meters that operate at the frequencies necessary for soil moisture and salinity measurements are typically bulky, require extensive calibration, expensive, and electrically invasive in that their presence greatly perturbs the desired measurement through stray capacitance and other effects.

Thus, the invention preferably uses diode voltage meters in their place. Diode voltage meters provide an output that is a direct current ("DC") voltage read by a DC voltage meter. The diode voltage meters are typically inexpensive and work well at high frequencies. Those of ordinary skill in the art are familiar with using diode detectors as AC voltage meters. In one embodiment of the sensor 20, diode voltage meters are used as they produce an easily measured DC output voltage, are inexpensive, work well at both high and low frequencies, and do not significantly perturb the measurement.

The diode voltage meter utilized in one embodiment of the present invention is unique because it is biased, adding a bias voltage $V_B$ 82 and bias resistor $R_B$ 81 to the standard diode voltage meter circuit, as shown in FIG. 2. This biasing dramatically improves the voltage meter performance by improving the linearity of the sensor 20, allowing for smaller AC voltages to be measured, and by removing the effects of variations in individual diodes and temperature effects. The presence of the bias voltage allows the output of the voltage meter 26, 27 or 28 to be measured in the absence of any AC signal being present in the circuit 40. The bias voltage, which is present at all times when the sensor 20 is powered, allows for the output of the voltage meter 26, 27 or 28 to be measured with no AC signal present, and the effects of temperature drift and variation in individual diode drop are determined by the fixed output level.

When the output of the diode voltage meter, is measured again, this time with an AC signal present, the difference in the outputs of the voltage meters 26, 27 and/or 28 essentially represents the AC signal value present without any errors introduced by variations in diode drop and temperature. Because of this difference approach, diodes do not need to be carefully characterized and matched within the circuit 40, thereby simplifying sensor manufacturing and reducing cost.

In addition, to obtain a separate temperature measurement, correction algorithms do not need to be used to account for temperature effects. Diode voltage meters in the absence of biasing do not allow for the measurement of AC signals much below 0.2V due to the voltage drop across the diode. The presence of the bias voltage allows AC voltages down to around 0.01V to be accurately measured which allows the sensor 20 to respond to a larger variation in $C_S$ and $R_s$. This allows the sensor 20 to be "tared" to capture the variation in components in the voltage meter and temperature drifts. The bias voltage also enables the voltage meters 26, 27 and 28 to respond to very small AC signals, and provide much more accurate measurements at low AC signal levels. Further, since the voltage meters 26, 27 and 28 are preferably tared, the individual voltage meters do not require carefully matched parts, thus making manufacturing easier.

Figure 9:
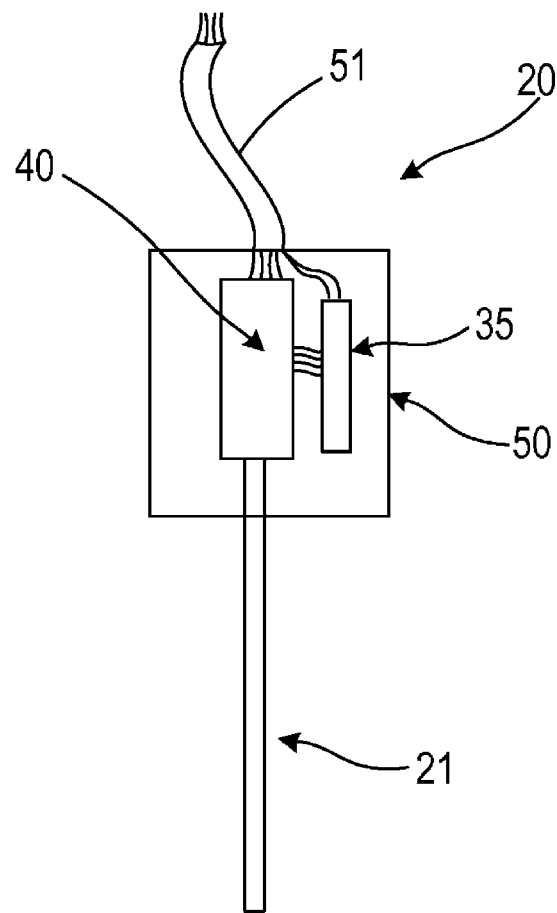
FIG. 9 is a schematic of an embodiment of a sensor apparatus of the present invention.
Figure 3:
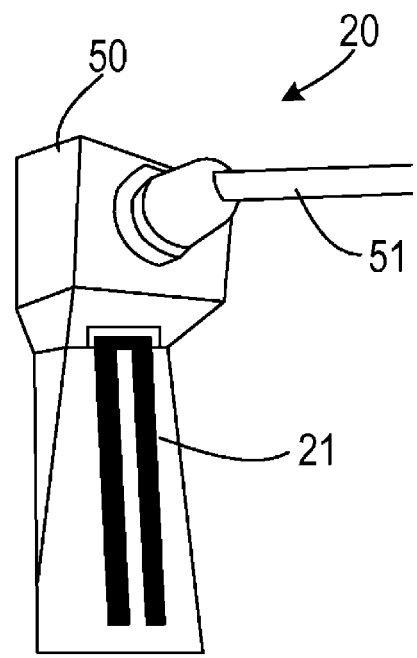
FIG. 3 is a perspective view of a sensor apparatus of the present invention.

FIG. 3 illustrates a preferred embodiment of a sensor apparatus 20 of the present invention. The sensor apparatus 20 is preferably pre-calibrated for typical sand, silt, or clay soils. The sensor apparatus 20 may need to be adjusted for other soils due to a possible difference in composition and placement. The sensor apparatus 20 has excellent accuracy and reliability. The sensor apparatus 20 can preferably provide a reading of +/−1.0% of a moisture reading from 0 to saturate at <5 dS/m conductivity and +/−3.0% of a moisture reading from 0 to saturation at >5 dS-10 dS/m conductivity. As for salinity, the sensor apparatus 20 of the present invention has a +/−2% of conductivity reading up to 5 dS/m (5 dS/m=30% seawater). The temperature reading is +/−1 degree Celsius from −10 degrees Celsius to +50 degrees Celsius. The measurement repeatability is preferably <<1%. The sensor apparatus 20 preferably includes a housing 50, a probe structure 21 and a cable 51 for power and communications with a control center. As shown in FIG. 9, the housing 50 preferably contains the circuit 40 and digital signal processor 35. The probe structure 21 extends from the housing 50, and cable 51 allows for connections to the circuit 40 and digital signal processor 35.

The present invention may be utilized with the system and method of Glancy, et al., U.S. Patent Publication Number 2006/0178847, published on Aug. 10, 2006, for an Apparatus And Method For Wireless Real Time Measurement And Control Of Soil And Turf Conditions (U.S. patent application Ser. No. 11/350,328 filed on Feb. 8, 2006), which is hereby incorporated by reference in its entirety.

The present invention provides a sensor apparatus 20 having a circuit 40 that allows for measuring the electrical conductivity and dielectric permittivity of a wide range of media. Specifically, these media include soils, water, grain, brackish waters, ices, and the like media.

As shown in FIG. 9, the housing 50 protects the circuitry from moisture and other hazards. The circuit 40 produces analog signals that are used to determine dielectric permittivity (and temperature if desired). A data reduction circuitry is optionally included and includes a microcontroller to measure the analog voltages and perform the calculations to determine the electrical properties and relate them if desired to other properties (such as soil moisture and soil salinity). A probe structure 21 preferably includes electrically conducting surfaces that can be inserted into the media of interest. The cable 51 allows for the calculated outputs to be sent to other instruments Alternatively, wireless or other communication protocols can be used without departing from the scope and spirit of the present invention.

The housing 50 is preferably composed of stainless steel or PVC. However, those skilled in the pertinent art will recognize that the housing 50 may be composed of other materials without departing from the scope and spirit of the present invention.

The circuit 40 converts the media's dielectric permittivity and conductivity to analog voltage signals that are used to calculate the electrical properties. These calculations are performed using the digital signal processor 35 in the sensor 20, or alternatively the analog voltage signals are transferred to an external instrument for the required calculations.

The digital signal processor 35 is used to measure the raw analog signals, convert them to a digital format, calculate electrical properties, calculate related properties (such as soil moisture and salinity) as well as control the oscillators (discussed below). The digital signal processor 35 can be used to output the calculated parameter digitally or in an analog format over the cable 51, or alternatively through the use of additional circuitry, wirelessly.

The probe structure 21 connects electrically to the circuit 40 and preferably includes at least two electrically conducting surfaces or structures. The probe structure 21 is inserted into the media to form a capacitor. The probe structure 21 is preferably composed of metal, printed circuit board material (with copper layer), or other materials.

The cable 51 allows power to be supplied externally as well as allowing for the output of the analog signals of the circuit 40. In an embodiment with the digital signal processor 35, the oscillators 24 and 25 are directly controlled and the cable 51 can be used to transmit the calculated electrical properties.

Figure 10:
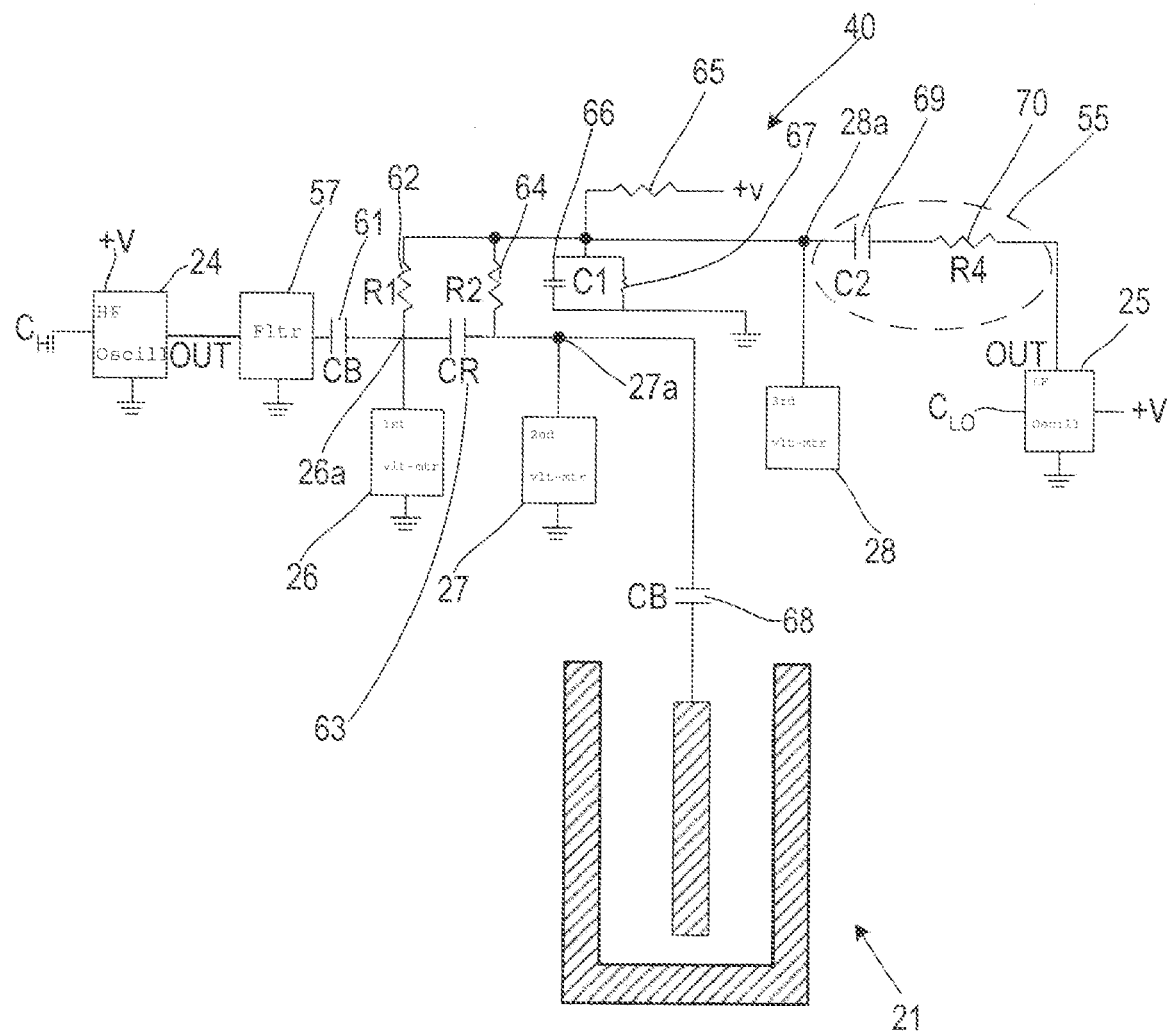
FIG. 10 is a circuit schematic of an embodiment of the sensor apparatus of the present invention.

As shown in FIG. 10, the sensing electronic circuitry 40 converts the soil dielectric permittivity and conductivity into analog signals as described below.

The circuit 40 preferably employs two oscillators, a high frequency oscillator 24 (125 MHz for example) and a low frequency oscillator 25 (10 MHz for example) powered by +V (a DC voltage), and which can be controlled (turned off and on) by a capacitor $C_{HI}$ and a capacitor $C_{LO}$, respectively. Those skilled in the pertinent art will recognize that oscillators with a wide range of operating frequencies can be used with the present invention without departing from the scope and spirit of the present invention. The oscillating electrical outputs appear at "OUT." A filter 57, which is connected to high frequency oscillator 24 is preferably a bandpass filter centered at the primary frequency of the high oscillator 24 and removes higher order harmonics to preferably produce a nearly sinusoidal output. Capacitor C2 69 and resistor R4 70 are connected to the low frequency oscillator 25 to form a low pass filter 55 (designated by dotted lines) which removes any higher order harmonics, specifically if the low oscillator 25 is a square wave oscillator.

Figure 10A:
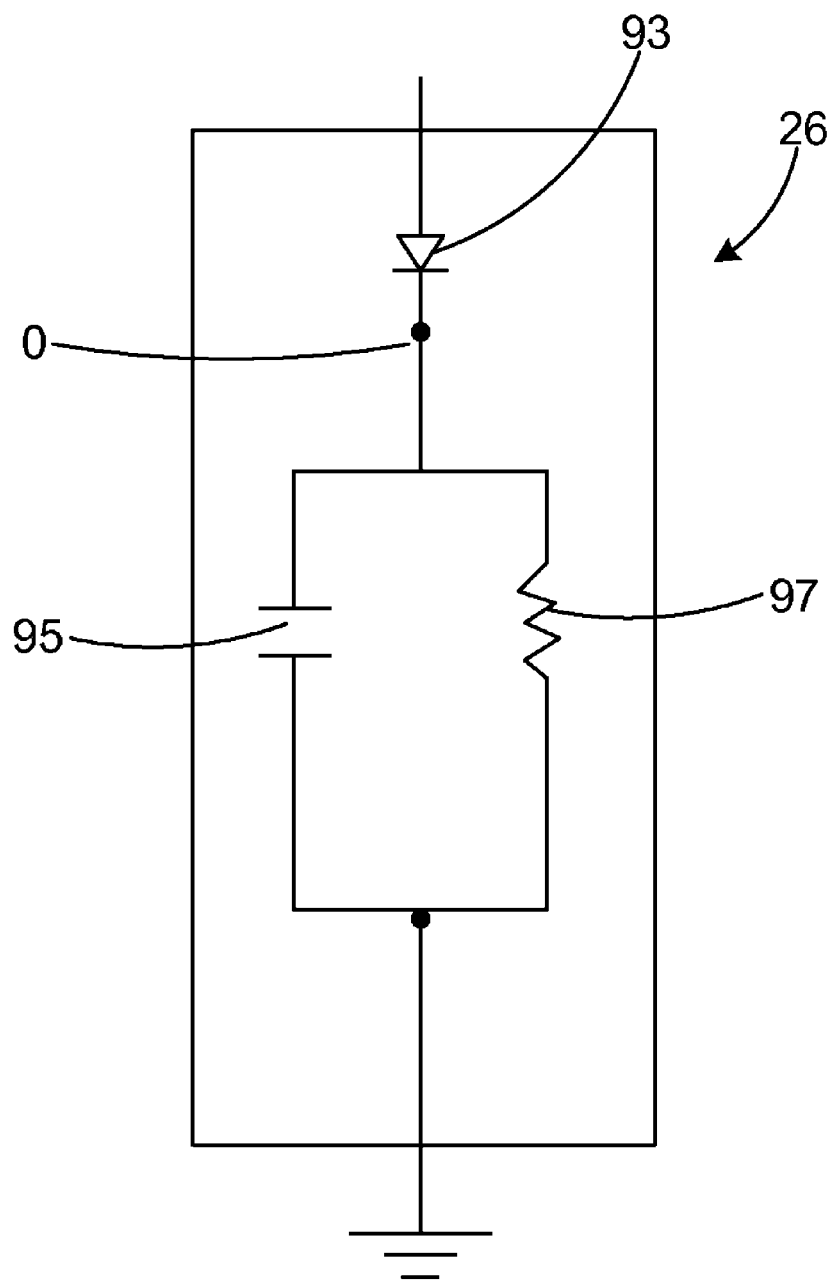
FIG. 10A is an isolated circuit diagram of a preferred voltage meter of the present invention.

A plurality of voltage meters 26, 27 and 28 are used to measure the AC level present at various points 26a, 27a and 28a in the circuit 40. As shown in FIG. 10A, each of plurality of meters 26, 27 and 28 preferably comprises a diode 93 connected with a capacitor 95 and resistor 97 in parallel (FIG. 10A only shows a voltage meter 26). The output "O" of each of the plurality of meters 26, 27 and 28 is preferably a direct current ("DC") voltage (measured between the diode and the capacitor and resistor) and is indicative of the amplitude of the AC stimulus present at the point 26a, 27a and 28a in the circuit 40 to which the other end of the diode 93 is connected.

A biasing network is formed by resistor R1 62, resistor R2 64, resistor R3 65, resistor R5 67 and capacitor C1 66. The biasing network ensures that even in the absence of any AC stimulus in the circuit 40, each of the voltage meters 26, 27 and 28 has a DC voltage present, thus providing a non-zero output for each of the voltage meters 26, 27 and 28. In addition, resistor R2 64 is also a conductivity reference element, which is described in greater detail below.

Two capacitors CB 61 and 68 ensure that the bias voltages are drained through the filter 57 as well as preventing any DC voltages from being present on the probe structure 21, which can result in deleterious galvanic reactions and electrode polarization. Capacitor CB 61 is selected to have a sufficiently high capacitance to have a negligible impedance at both the high and low frequencies employed so as to negligibly affect the measurements.

A capacitor CR 63 is preferably a precision capacitor used to form a reference element for the dielectric permittivity measurements.

The sensor 20 preferably has two main paths through which the electrical measurements are made. First, the high frequency path of the soil moisture circuit 22 (used to measure the dielectric permittivity) is through the high frequency oscillator 24, the filter 57, the capacitor CB 61, by the first voltage meter 26, the capacitor CR 63, by the second voltage meter 27, the capacitor CB 68 and into the probe structure 21. Second, the low frequency path, or the soil salinity circuit 23, is through low frequency oscillator 25, the resistor R4 70, the capacitor C2 69, by the third voltage meter 28, resistor R2 64, by the second voltage meter 27, capacitor CB 68 and into the probe structure 21. By judicious choice of the elements of the circuit 40, the high and low frequency paths can share many elements of the circuit 40 as well as the probe structure 21, while having very little effect on the other pathway.

A preferred measurement can be made in the following manner and the tables of FIGS. 4 and 6 list the measurement values. Those skilled in the pertinent art will recognize that different procedures are possible without departing from the scope and spirit of the present invention. First, with both the high frequency oscillator 24 and the low frequency oscillator 25 deactivated, the outputs of the first voltage meter 26, the second voltage meter 27, and the third voltage meter 28 are measured, at points 26a, 27a and 28a respectively, and referred to respectively as O1, O2, O3. The high frequency oscillator 24 is then activated and the first voltage meter 26 and the second voltage meter 27 are measured, at points 26a and 27a respectively, and referred to respectively as O1' and O2'. The high frequency oscillator 24 is then deactivated and the low frequency oscillator 25 is activated and the second voltage meter 27 and the third voltage meter 28 are measured, at points 27a and 28a respectively, and referred to respectively as O2" and O3". In the case where an oscillator 24 or 25 is deactivated, the voltage meter output is indicative of a "baseline" voltage meter output. When an oscillator 24 or 25 is activated, the voltage meter is indicative of the baseline level plus the AC stimulus amplitude present at the measurement point 26a, 27a and/or 28a.

The measured voltages can then be used to calculate the following ratios: $RP=(O2'-O2)/(O1'-O1)$ and $RC=(O2''-O2)/(O3''-O3)$.

The probe structure 21 forms a capacitance CS and conductivity CONDS determined by the dielectric permittivity and electrical conductivity of the sample the conducting structure is placed in as well as geometrical factors (spacing, size, geometry, etc. of conducting surfaces). The two circuit pathways form bridge circuits (CR and CS on the high frequency path) and (R2 and CONDS on the low frequency path). To the first order it can be shown that:

$$CS/(CS+CR)=RP \text{ and } CONDS/(CONDS+R2)=RC$$

This allows one to solve for the dielectric permittivity of the sample and its conductivity when the scaling factor introduced by the geometrical factors of the sensing structure are determined, as CR and R2 are known values. Furthermore, these calculations can be refined to remove high order effects (finite electrical length, pathway coupling, etc.) through calibration with known samples.

Data reduction circuitry can be used to automate this procedure as well as perform the required calculations. A suitable data reduction circuit has been developed and tested.

The circuit 40 contains many novel features that greatly improve accuracy, cost, and practicality. They include novel biased detectors, a novel biasing scheme, a novel differential measurement scheme, a novel dual frequency scheme, novel matched reference elements, and novel power supply variation rejection.

In a preferred embodiment, the diode based voltage meters 26, 27 and 28 are always forward biased regardless of the signal level. Depending on diode type, at forward drops of less than about 0.3V or so, little or no current flows. Small AC signals with amplitudes less than 0.3V in amplitude would be undetectable without the biasing employed.

The circuitry has been designed to allow the biasing to be provided to the voltage meters 26, 27 and 28 while simultaneously allowing an affected measurement to be made. This is accomplished through the use of blocking capacitors and selected values for the biasing circuitry.

Because the outputs of the voltage meters 26, 27 and 28 are measured with and without AC stimulus being present non-matching diodes 85 are used, as the ratios RP and RC are essentially independent of the individual diode drops. Furthermore, the temperature drift of the diodes is automatically nulled-out by this procedure.

The present invention measures conductivity at low frequencies so that capacitive effects do not distort the measurement and dielectric permittivity at high frequencies so that conductive effects do not distort the measurement. This design allows the use of two frequencies in one sensor with the same probe structure 21 allowing for improved accuracy in a wide range of media.

The bridge element in the dielectric permittivity measurement is a capacitor, CR. It can be shown that using a capacitor as a reference element offers superior rejection of distortion due to conductivity effects. Likewise, the bridge element in the conductivity measurement is a resistor which offers superior rejection of distortion due to capacitive effects.

As the measurements is "ratio metric", the output level of oscillators 24 and 25 is essentially linear with power supply voltage, and the baseline voltage meter level is measured (and accounted for in the calculations) the calculations of electrical parameters is highly insensitive to variations in power supply voltage over a significant range allowing for a low cost, simple power supply to be used.

Figure 4:
FIG. 4 is a table of experimental results on sand showing measured values in a drying experiment with water percentage as expressed percentage by volume of water in a sand sample.
Figure 5:
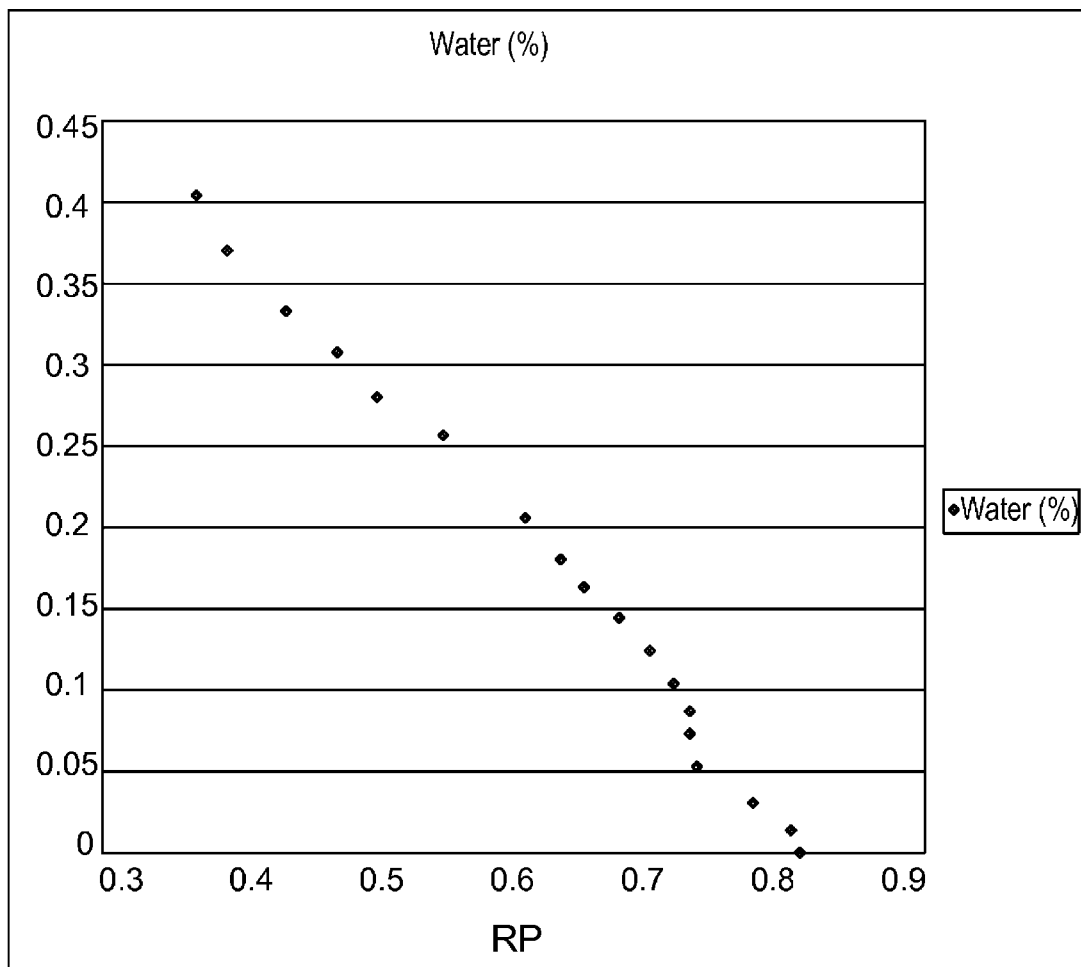
FIG. 5 is a graph of a calibration curve illustrating water content as a function of RP.

As shown in FIG. 4, a table 200 lists values for voltage meter measurements O1, O2, O3, O1', O2', O2" and O3". Also listed are values for the calculations RP and RC as well as a percentage of moisture (water %) in the media. FIG. 5 illustrates a graph 202 with a calibration curve of the water % (Y axis) as a function of RP (X axis). RP is used to calculate capacitance and is correlated to soil moisture.

Figure 6:
FIG. 6 is a table of experiments in aqueous saline solutions of known conductivity ranging from 0.1 to 4.96 dS/m and replicated for four different sensors.
Figure 7:
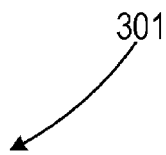
FIG. 7 is a continuation of the Table in FIG. 6.
Figure 8:
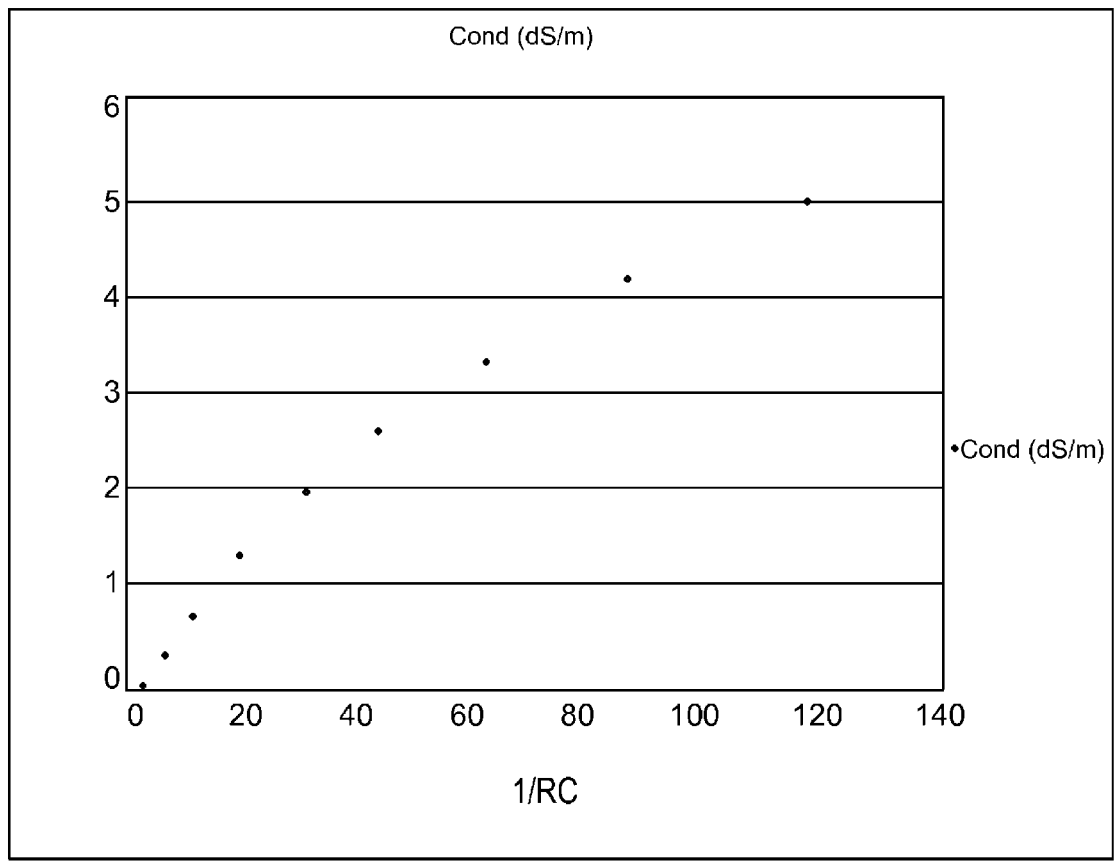
FIG. 8 is a graph of a calibration curve showing variation in 1/RC with increasing sample conductivity.

As shown in FIG. 6, a table 300 lists values for voltage meter measurements O2, O3, O2" and O3". Table 300 also lists values for RC and the type of media sensors for four different sensors. The type of media is aqueous saline solutions of known conductivity spanning 0.1 to 4.96 dS/m. Each sensor set is for a different type of media. Each sensor set includes values for each of the four different sensors designated 3, 5, 8 and 11 in the table 300. As shown in FIG. 7, a table 301 lists the average RC value and the standard deviation value from the values in table 300 of FIG. 6. FIG. 8 illustrates a graph 302 showing a calibration curve of the variation in 1/RC (X axis) with increasing sample conductivity (Y axis).

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

I claim as my invention:

1. A sensor device comprising:
    a housing;
    a sensing circuitry positioned within the housing, the sensing circuitry comprising a high frequency oscillator, a reference capacitor connected in series to the high frequency oscillator, and a first voltage meter located between the high frequency oscillator and the reference capacitor, and the sensing circuitry comprising a low frequency oscillator, a reference resistor connected in series to the low frequency oscillator, and a second voltage meter located between the low frequency oscillator and the reference resistor;
    a data reduction circuitry positioned within the housing, the data reduction circuitry comprising a microcontroller to measure analog voltages and perform calculations to determine a plurality of electrical properties and correlate the plurality of electrical properties to soil moisture and soil salinity;
    a sensing structure positioned within the housing and connected to the sensing circuitry wherein the sensing structure comprises a plurality of electrically conducting surfaces for contact with a material; and
    a wireless communication circuit for wirelessly transmitting a plurality of calculated output values for soil moisture and soil salinity from the sensor.

2. The sensor device according to claim 1 wherein the sensing circuitry generates analog signals for determining dielectric permittivity.

3. The sensor device according to claim 1 wherein the material comprises soil, water, grain, brackish water and ices.

4. The sensor device according to claim 1 wherein the housing is composed of stainless steel.

5. The sensor device according to claim 1 wherein the housing is composed of PVC.

* * * * *